US00PP32375P2

(12) United States Plant Patent
Jones

(10) Patent No.: US PP32,375 P2
(45) Date of Patent: Oct. 20, 2020

(54) ***AGASTACHE* PLANT NAMED 'ASUMO02-0'**

(50) Latin Name: ***Agastache* hybrid**
Varietal Denomination: ASUMO02-0

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 0 days.

(21) Appl. No.: 16/602,644

(22) Filed: Nov. 12, 2019

(51) Int. Cl.
*A01H 5/02* (2018.01)
*A01H 6/50* (2018.01)

(52) U.S. Cl.
USPC ..... Plt./399
CPC ..... *A01H 6/50* (2018.05)

(58) Field of Classification Search
USPC ..... Plt./399
CPC ..... A01H 6/50; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Agastache* plant named 'ASUMO02-0' is disclosed, characterized by deep red flowers, and increased branching. Plants are vigorous and produce densely flowering racemes. The new cultivar is an *Agastache*, suitable for ornamental garden purposes.

2 Drawing Sheets

Latin name of the genus and species: *Agastache* hybrid.
Variety denomination: 'ASUMO02-0'.

BACKGROUND OF THE INVENTION

The new cultivar is the result of a planned breeding program by the inventor. The crossing of two unnamed, unpatented, proprietary varieties of *Agastache* was made in June 2017 in Santa Paula, Calif. 'ASUMO02-0' was found and selected in August 2017.

The first asexual propagation of 'ASUMO02-0' occurred in September 2018 by vegetative terminal cuttings at a nursery in Santa Paula, Calif. Subsequent propagation has shown that the unique features of this cultivar are stable and reproduced true to type in several successive generations.

SUMMARY OF THE INVENTION

The following are the unique combination of characteristics of this new cultivar when grown under standard horticultural practices in Santa Paula, Calif.:

1. Deep red flowers.
2. Increased branching.
3. Densely flowering raceme.
4. Vigorous plants.

COMPARISON TO PARENT VARIETIES

'ASUMO02-0' is similar in most horticultural characteristics to the seed parent. Plants of the new cultivar 'ASUMO02-0' however differ in the following:

1. The new variety has more flowers per inflorescence than the seed parent.
2. The new variety has deep red flowers, while the seed parent has pink flowers.

'ASUMO02-0' is similar in most horticultural characteristics to the pollen parent. Plants of the new cultivar 'ASUMO02-0' however differ in the following:

1. The new variety has greater plant vigor than the pollen parent.

2. The new variety is a denser plant with more branches than the pollen parent.
3. The new variety has darker red flowers than the pollen parent.

COMMERCIAL COMPARISON

'ASUMO02-0' can be compared to the commercial variety *Agastache* 'Acapulco Red', unpatented. Plants of the two cultivars are similar in most horticultural characteristics. Plants of the new cultivar 'ASUMO02-0', however, differ in the following:

1. The new variety has deeper red flowers than this comparator.
2. The new variety has more branches than this comparator.
3. The new variety is a more vigorous plant than this comparator.
4. Flowers of the new variety are stacked more tightly on the raceme than flowers of this comparator.

BRIEF DESCRIPTION OF THE PHOTOGRAPHS

'ASUMO02-0' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new hybrid *Agastache*.

DETAILED BOTANICAL DESCRIPTION

Figure 1:
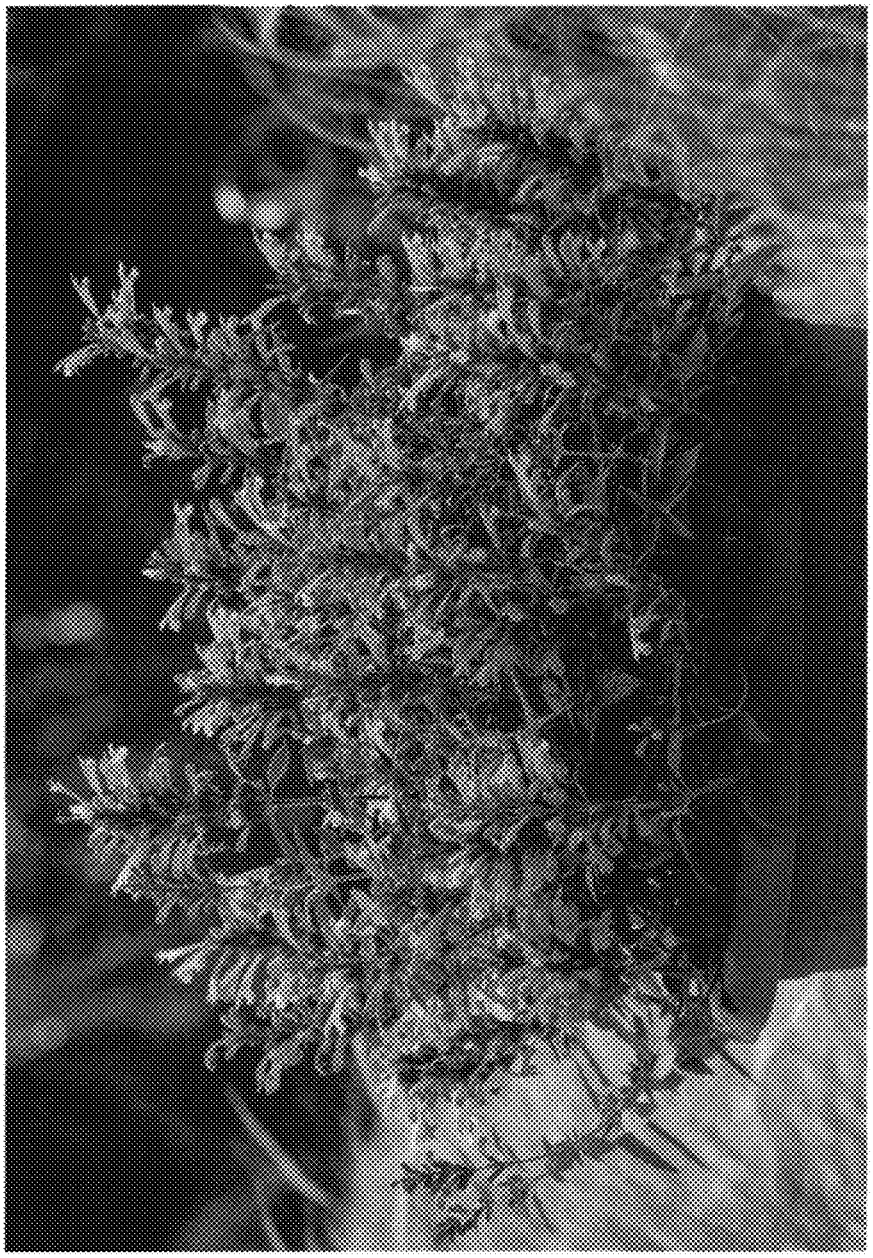
FIG. 1 shows a plant of the new variety at about 8 months old from a rooted cutting grown in a greenhouse in Santa Paula, Calif. during Spring.
Figure 2:
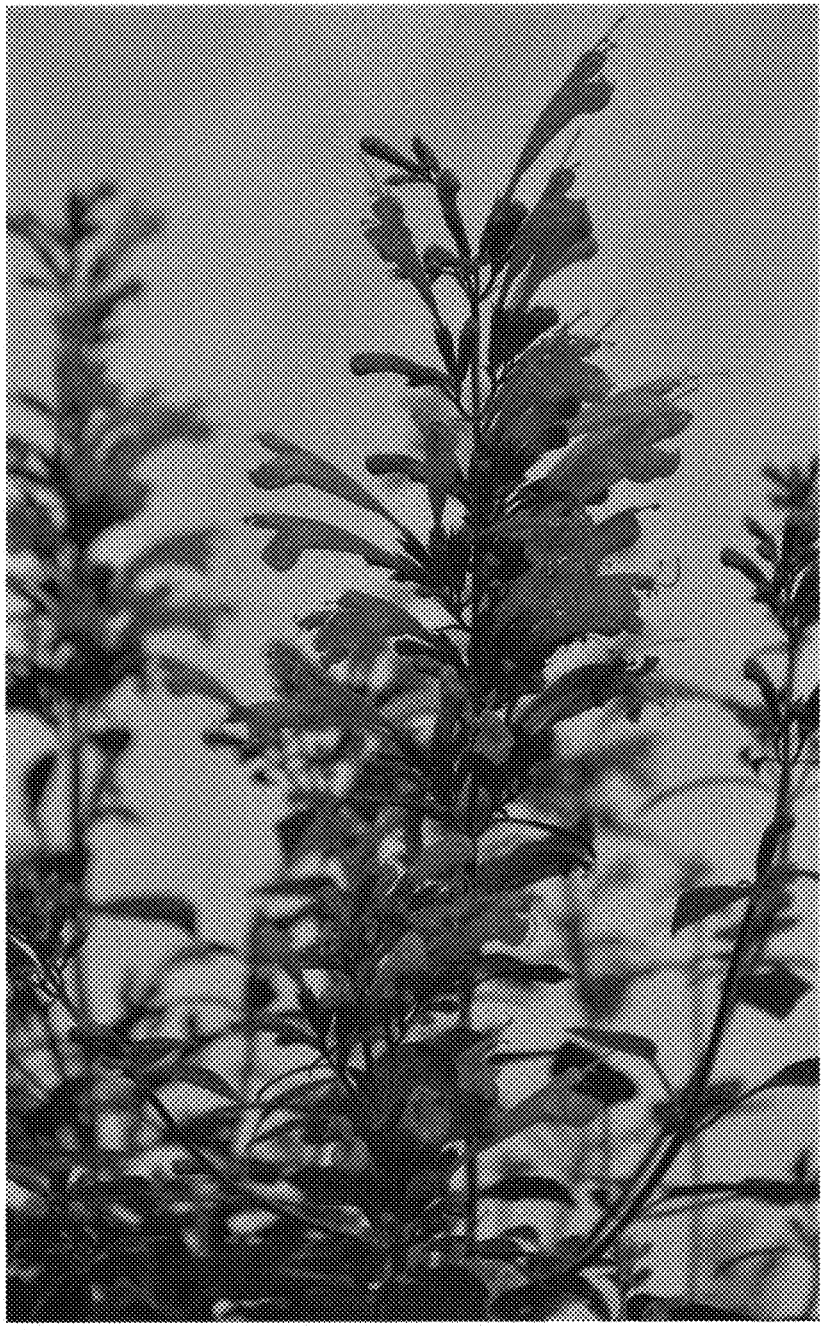
FIG. 2 shows a close-up view of the inflorescence.

The following is a detailed description of the botanical characteristics of the new and distinct hybrid *Agastache* known by the denomination 'ASUMO02-0'. The detailed description was taken of an 8 month old plant in Santa Paula, Calif. in 2019. For each measurable character, ten random measurements were recorded and used to derive averages and characteristic ranges. All colors cited herein refer to The Royal Horticultural Society Colour Chart (R.H.S.), 2007 Edition.

Botanical classification: *Agastache* 'ASUMO02-0'.

PROPAGATION

Time to initiate roots: About 20 days at approximately 20 to 22° C.

Root description: Fine, densely fibrous.

Time to produce a rooted cutting: About 21 days at 22° C.

PLANT

Growth habit: Upright to outwardly arching annual.

Pot size of plant described: 10 inch.

Height: Approximately 35 cm to top of flowering plane, approximately 22 cm to top of foliage plane.

Plant spread: Approximately 45 cm.

Growth rate: Rapid.

Branching characteristics: Free-branching.

Length of primary lateral branches: Approximately 10 to 14 cm, foliage section only.

Diameter of lateral branches: Approximately 0.3 cm.

Quantity of lateral branches: Approximately 4 to 8 branches emerge from a pinch.

Stem:

*Color*.—Near RHS Green 143C.

*Pubescence*.—Very short, dense pubescence.

*Other stem characteristics*.—Quadrangular.

Internode length: Averages between 3.5 to 5 cm.

Age of plant described: Approximately 20 weeks from 3 rooted cuttings.

FOLIAGE

Leaf:

*Arrangement*.—Opposite.

*Quantity*.—Approximately 8 to 14 fully expanded leaves per main branch.

*Average length*.—Approximately 4.8 cm.

*Average width*.—Approximately 1.9 cm.

*Shape of blade*.—Deltoid.

*Apex*.—Acute.

*Base*.—Cordate to rounded.

*Attachment*.—Stalked.

*Margin*.—Nearly entire, typically 3 to 4 serrations per side.

*Texture of top surface*.—Glabrous.

*Texture of bottom surface*.—Glabrous.

*Color*.—Young foliage upper side: Near RHS Green 137A. Young foliage under side: Near RHS Green 138A. Mature foliage upper side: Near RHS Green 137A. Mature foliage under side: Near RHS Green 138A.

*Venation*.—Type: Pinnate. Venation color upper side: Near RHS Yellow-Green 144B. Venation color under side: Near RHS Green 138C.

*Petiole*.—Average Length: Approximately 1.3 cm. Diameter: Approximately 0.1 cm. Color: Near RHS Green 138A.

FLOWER

Natural flowering season: Flowering begins early Spring and continues through late Summer.

Inflorescence type and habit: Flowers arranged in racemes. Individual flowers self-cleaning, calyx persistent.

Flower longevity on plant: Individual flowers approximately 8 days on the plant without significant color loss or other degradation.

Quantity of flowers: Between 15 and 30 fully opened flowers per blooming spike, at one time; about 40 blooming spikes per plant.

Inflorescence size:

*Diameter*.—Approximately 8.5 cm.

*Height*.—Average range 10 to 16 cm.

Peduncle:

*Length*.—Average range 5 to 7 cm.

*Diameter*.—3 mm.

*Color*.—Near RHS Green 138A.

*Orientation*.—Straight.

*Texture*.—Pubescent and ridged.

*Strength*.—Strong.

Pedicel:

*Length*.—Average range 2 to 5 mm.

*Diameter*.—1 mm.

*Color*.—Near RHS Greyed-Purple N186C.

*Orientation*.—Straight.

*Texture*.—Pubescent.

*Strength*.—Soft and flexible.

Corolla:

*Petal arrangement*.—The corolla is highly fused, zygomorphic, bilabiate. 1 upper lip with 2 lobes, and 2 smaller lateral petals with single lobes and 2 slightly larger highly fused lobes forming a lower lip.

*Margin*.—Entire.

*Petal apex shape*.—Obtuse.

*Entire corolla length*.—Approximately 3 cm.

*Entire corolla width*.—Approximately 1.3 cm.

*Attachment aspect*.—About 75° to stem.

*Persistence*.—Non-persistent.

*Fragrance*.—Very aromatic.

Petal:

*Length*.—Upper lip Approximately 0.5 cm, lower lip Approximately 0.7 cm. Laterals Approximately 0.4 cm.

*Width*.—Upper lip Approximately 0.6 cm, lower lip approximately 0.8 cm, laterals Approximately 0.4 cm.

*Texture*.—Glabrous.

*Tube*.—Length: About 2.6 cm. Width: About 1 cm at widest point.

Color:

*Petals*.—When opening: Interior surface: Near RHS Red 47C. Exterior surface: Near RHS Red 50B. Fully opened: Interior surface: Near RHS Red 50A. Exterior surface: Near RHS Red 50B. Fading: Interior surface: Near RHS Red 50B. Exterior surface: Near RHS Red 50C.

Floral tube:

*When opening*.—Interior surface: Near RHS Red 52D. Exterior surface: Near RHS Red 52C.

*Fully opened*.—Interior surface: Near RHS Red 52D. Exterior surface: Near RHS Red 54B.
*Fading*.—Interior surface: Near RHS Red 53D. Exterior surface: Near RHS Red 54A.

Bud:
*Shape*.—Curved ovoid.
*Length*.—Approximately 1.4 cm.
*Diameter*.—Approximately 0.4 cm.
*Color*.—Near RHS Red 47A.

Calyx:
*Length*.—Approximately 1.4 cm.
*Diameter*.—Approximately 0.2 cm.
*Shape*.—Tubular.

Sepals:
*Shape*.—5 sepals fused to form a tube.
*Apex*.—Highly acute.
*Margin*.—Entire.
*Texture*.—Pubescent. Ridged.
*Color*.—Near RHS Green 137C, flushed near apex Greyed-Purple N186C.
*Persistence*.—Persistent.

REPRODUCTIVE ORGANS

Stamens:
*Number*.—4.
*Filament length*.—Approximately 2.2 cm lower 20% fused to petals.
*Filament color*.—Near RHS Purple 75A.

Anthers:
*Shape*.—Elliptic.
*Length*.—Approximately 1 mm.
*Color*.—Near RHS Greyed-Purple N186A.
*Pollen*.—Scant.
*Pollen color*.—Near RHS Yellow-White 158D.

Pistil:
*Number*.—1.
*Length*.—Approximately 3.6 cm, not fused to floral parts.
*Style*.—Length: Approximately 3.4 cm. Color: Near RHS White 155C, uppermost section flushed near Red-Purple 64C.
*Stigma*.—Shape: Two-parted cleft. Color: Near RHS Purple N79C. Ovary color: Near RHS Yellow-White 158A.

OTHER CHARACTERISTICS

Disease and pest resistance: Not observed to be susceptible nor resistant to normal diseases and pests of *Agastache*.
Temperature tolerance: The new variety tolerates temperatures between 0 to 40° C.
Fruit/seed production: Not observed.

What is claimed is:

1. A new and distinct cultivar of *Agastache* plant named 'ASUMO02-0' as herein illustrated and described.

* * * * *